(12) United States Patent
Isaza et al.

(10) Patent No.: US 8,579,912 B2
(45) Date of Patent: Nov. 12, 2013

(54) SACROILIAC JOINT FUSION ALIGNMENT GUIDE

(75) Inventors: Jorge Eduardo Isaza, Baton Rouge, LA (US); Bryan S. Jones, West Roxbury, MA (US); Katherine H. Herard, Harrisville, RI (US); Richard Techiera, North Dartmouth, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 12/562,521

(22) Filed: Sep. 18, 2009

(65) Prior Publication Data

US 2010/0010496 A1    Jan. 14, 2010

Related U.S. Application Data

(62) Division of application No. 11/406,888, filed on Apr. 19, 2006, now abandoned.

(51) Int. Cl.
*A61F 2/46* (2006.01)

(52) U.S. Cl.
USPC ............................. 606/104; 606/86 R; 606/96

(58) Field of Classification Search
USPC .................................................. 606/96, 104
See application file for complete search history.

(56) References Cited

U.S. PATENT DOCUMENTS

| | | | |
|---|---|---|---|
| 4,383,527 A | 5/1983 | Asnis et al. | |
| 4,450,835 A | 5/1984 | Asnis et al. | |
| 4,537,185 A | 8/1985 | Stednitz | |
| 4,763,548 A | 8/1988 | Leibinger et al. | |
| 5,242,444 A | 9/1993 | MacMillan | |
| 5,334,205 A * | 8/1994 | Cain | 606/96 |
| 5,649,931 A | 7/1997 | Bryant et al. | |
| 5,688,284 A | 11/1997 | Chervitz et al. | |
| 5,968,050 A * | 10/1999 | Torrie | 606/87 |
| 6,189,422 B1 | 2/2001 | Stihl | |

(Continued)

OTHER PUBLICATIONS

Stryker Trauma, "Hip Fracture/Internal Fixation, The Asnis III Cannulated Screw System," retrieved online at http://69.20.14.147/trauma/hipfracture/asnis_home.php, 2 pages (2004).

*Primary Examiner* — Eduardo C Robert
*Assistant Examiner* — Nicholas Plionis
(74) *Attorney, Agent, or Firm* — Nelson Mullins Riley & Scarborough LLP

(57) ABSTRACT

A device and method for defining a trajectory for instruments in a sacroiliac joint fusion procedure employs a handle and two movable guidance arms that are separated by an adjustable distance. The first guidance arm has a substantially straight pronged distal end terminating in a first prong, a second prong and a space between the first prong and second prong defining a first point in a straight trajectory for inserting screws into a sacroiliac joint. The guidance arm forms a receiving bore on a distal end thereof to define a second point in the trajectory. The pronged distal end is inserted through a posterior incision in the patient into a cored-out sacroiliac joint, with the second guidance arm outside the body, and the orientation of the alignment guide is adjusted by pivoting the alignment guide about the pronged distal end to determine a suitable trajectory. Instruments and implements are placed along the trajectory and guided by the alignment guide to drill screw holes and insert screws used in the sacroiliac joint fusion procedure into the screw holes.

6 Claims, 22 Drawing Sheets

(56) References Cited

U.S. PATENT DOCUMENTS

| | | | |
|---|---|---|---|
| 6,547,795 B2 * | 4/2003 | Schneiderman | 606/96 |
| 6,635,059 B2 | 10/2003 | Randall et al. | |
| 6,669,698 B1 * | 12/2003 | Tromanhauser et al. | 606/86 A |
| 7,316,704 B2 * | 1/2008 | Bagaoisan et al. | 606/213 |
| 7,396,360 B2 * | 7/2008 | Lieberman | 606/247 |
| 7,648,509 B2 * | 1/2010 | Stark | 606/90 |
| 2002/0087161 A1 * | 7/2002 | Randall et al. | 606/73 |
| 2008/0009861 A1 * | 1/2008 | Stark | 606/61 |

\* cited by examiner

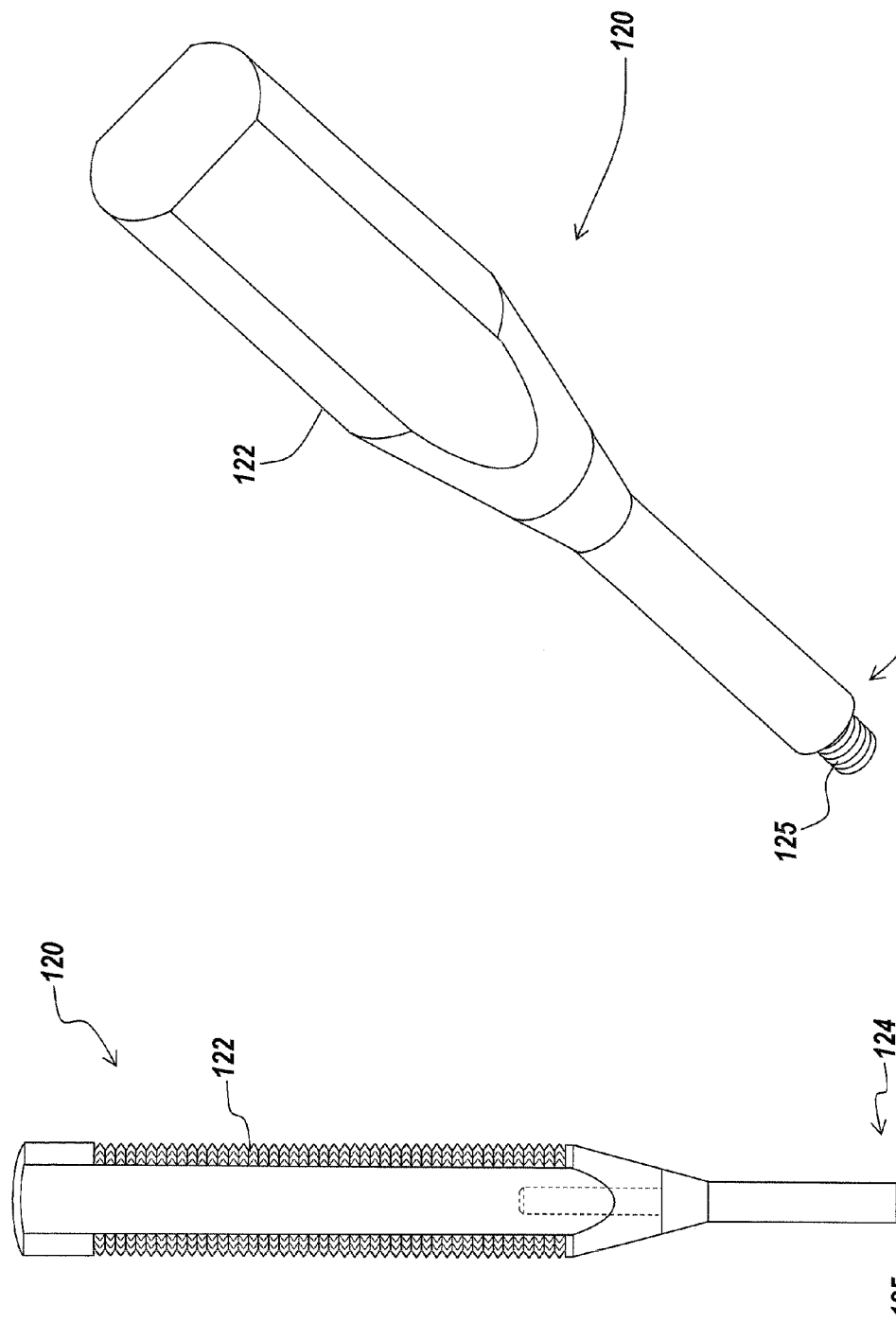

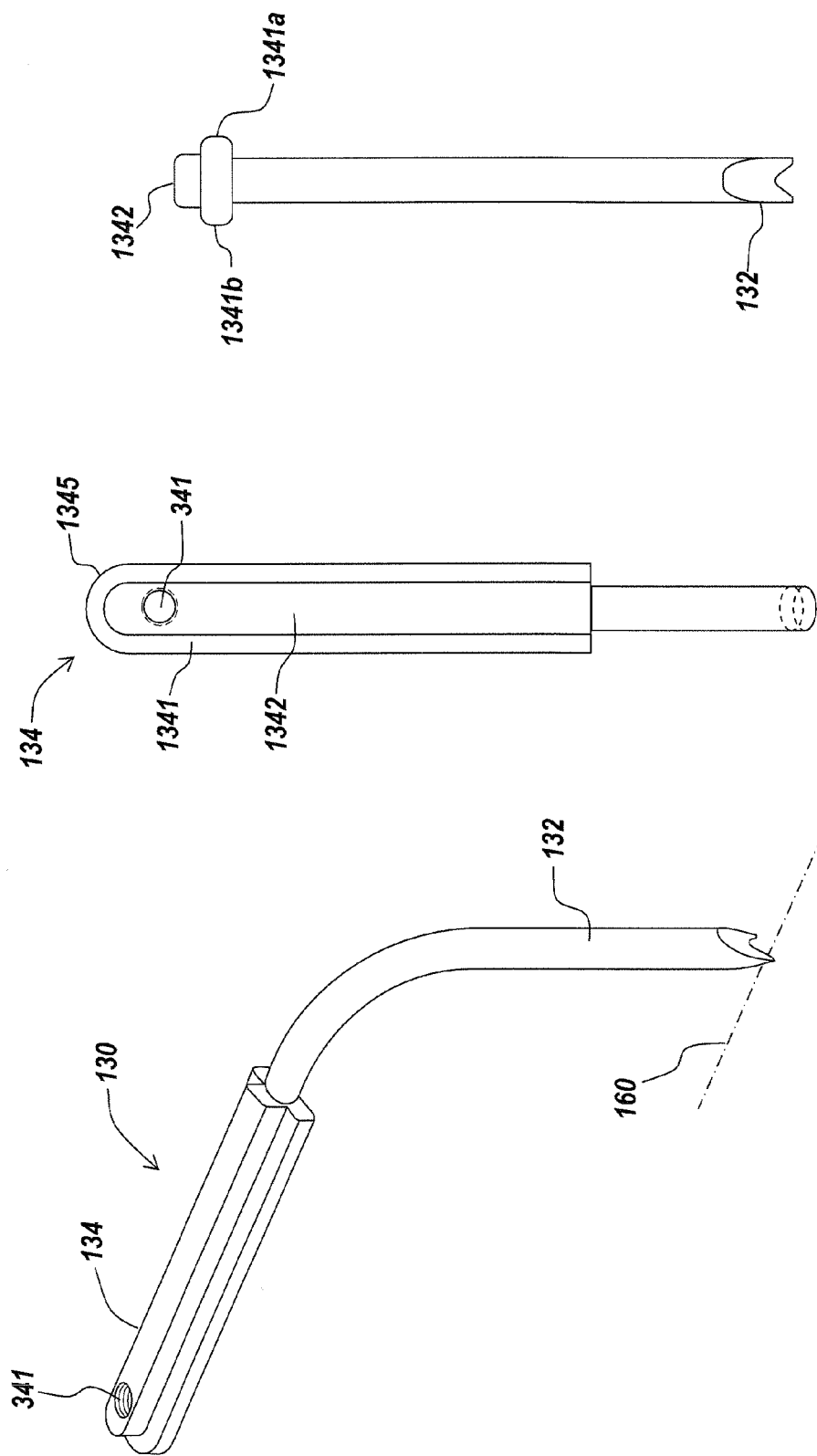

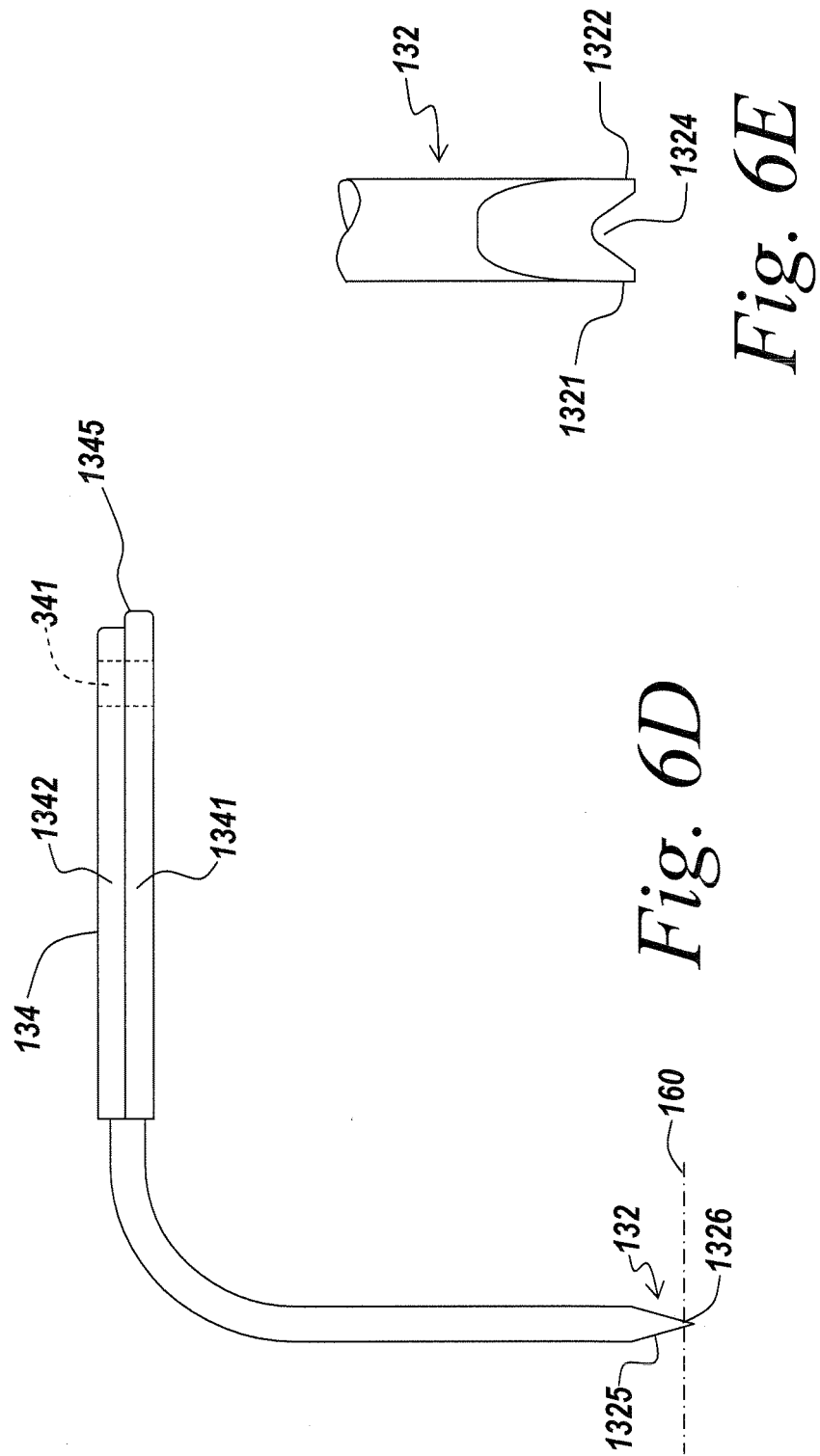

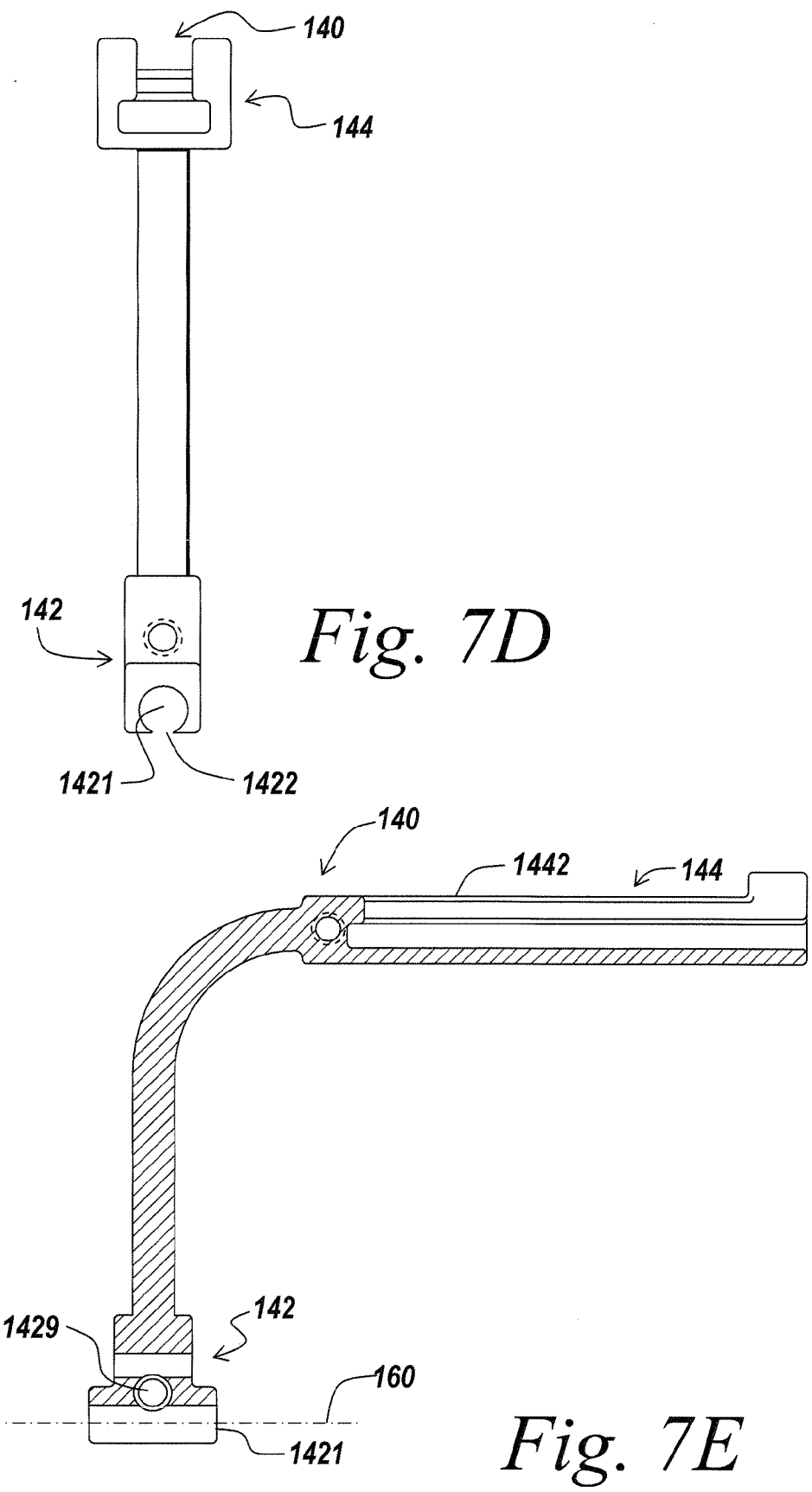

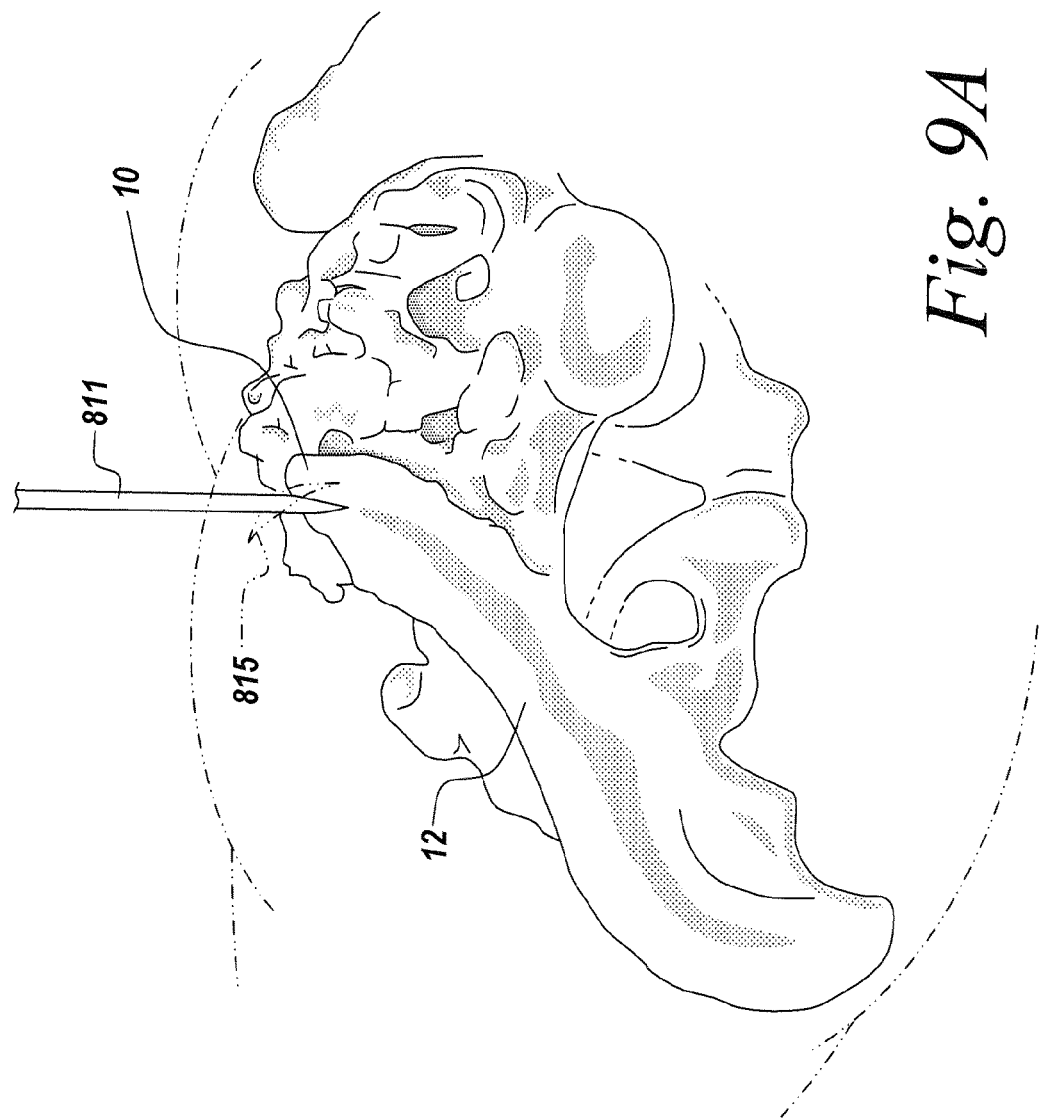

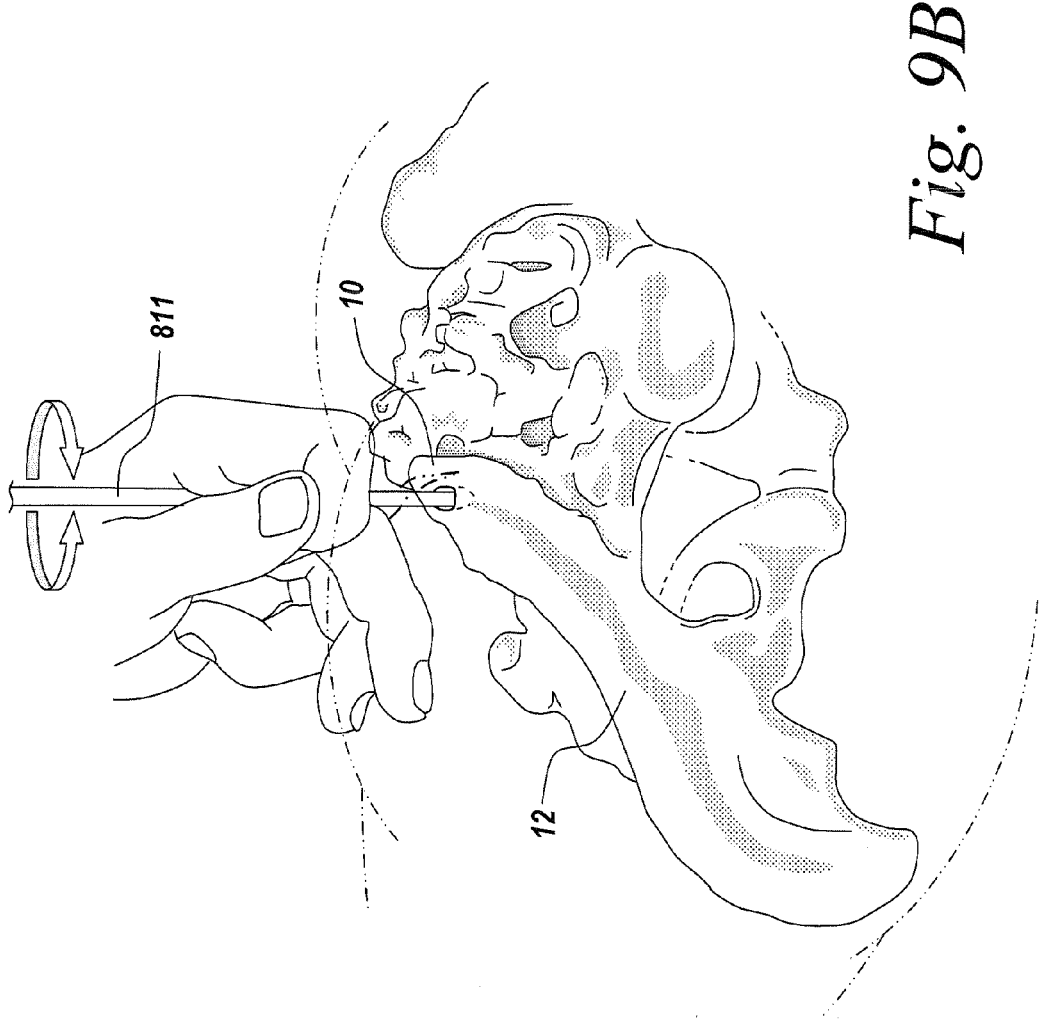

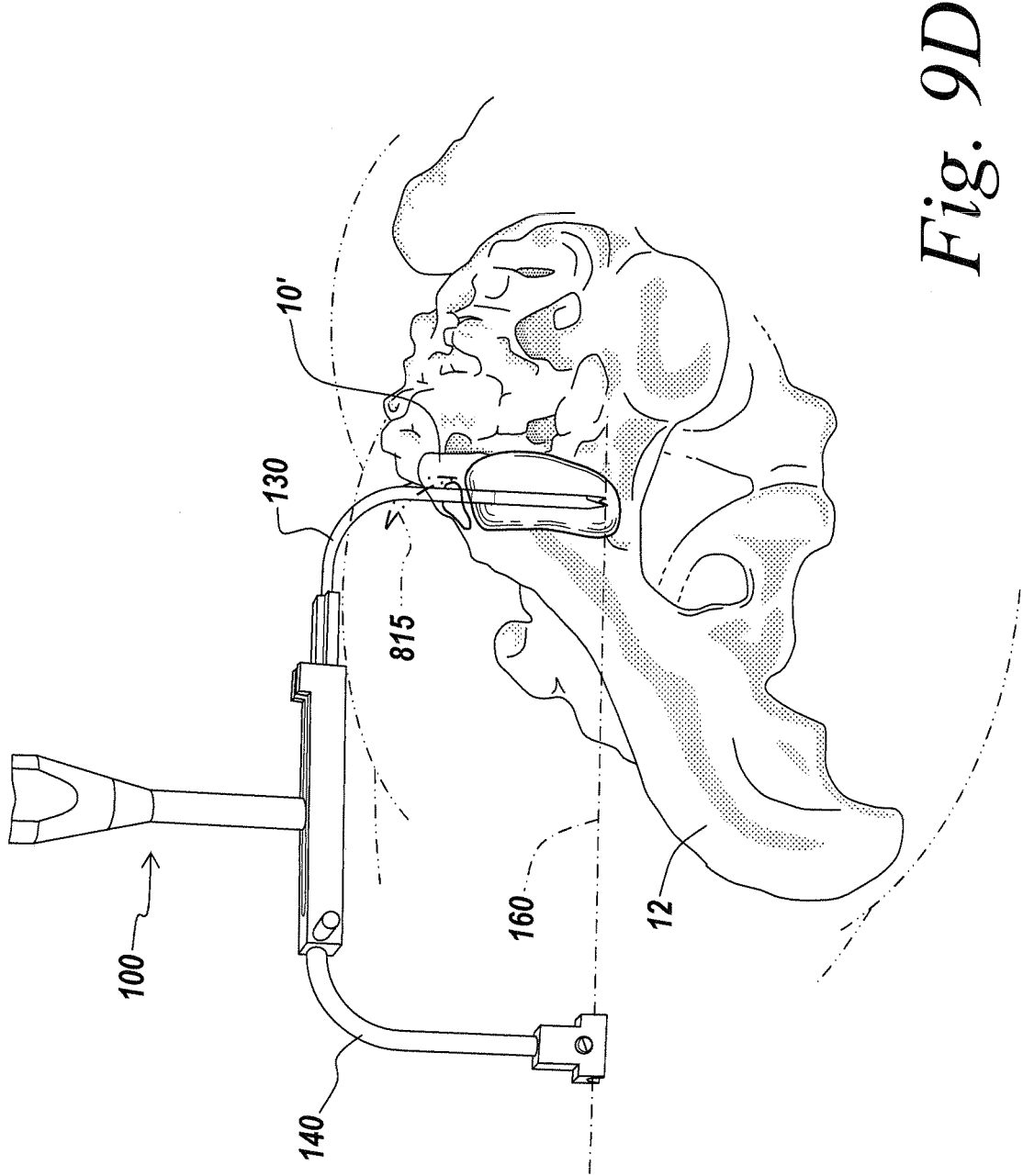

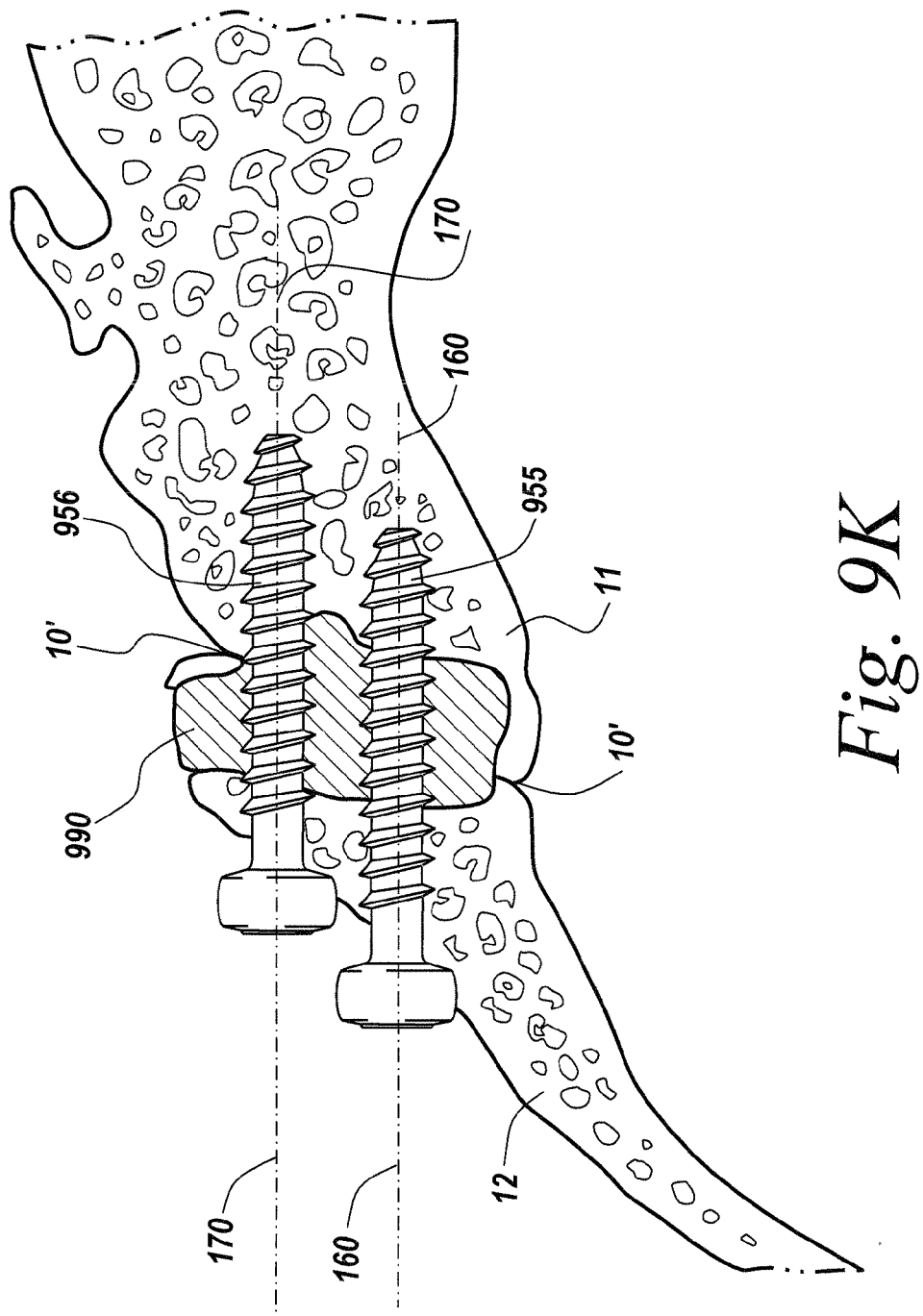

SACROILIAC JOINT FUSION ALIGNMENT GUIDE

RELATED APPLICATION

This application is a divisional application, of U.S. patent application Ser. No. 11/406,888, filed Apr. 19, 2006.

FIELD OF THE INVENTION

The present invention relates to a device and method for applying screws to fuse a sacroiliac joint in a patient.

BACKGROUND OF THE INVENTION

The sacroiliac (SI) joint 10 is located between the sacrum 11 and the hip bones 12, known as the ilium, in the human body, as shown in FIG. 1, and functions to transmit forces from the spine 14, including vertebrae 14a, intervertebral discs 14b and the coccyx 14c, to the lower extremities. The sacroiliac joint 10 is supported by ligaments and muscle. The sacroiliac joint 10 can degenerate over time, requiring a fusion procedure to stabilize the degenerated segment. For example, one condition, degenerative sacroiliitis, results in a narrow joint space with bone spur formation. Iatrogenic (i.e., induced by treatment) procedures, such as iliac bone graft damaging ligaments of the joint and/or previous fusions, can also cause degeneration, requiring sacroliac joint fusion. Alternatively, infection, ligamentous disruption due to pregnancy, and/or trauma causing fracture dislocation may require a sacroiliac joint fusion procedure to provide sufficient stabilization to allow the patient to achieve a normal lifestyle.

Traditionally, surgeons use screws, often with the combination of rods, to link the sacroiliac joint together. A standard sacroiliac stabilization procedure consists of the following steps: a posterior exposure to the spine, the removal of degenerated sacroiliac joint material, the posterior placement of a stabilizing screw/joint construct, or the lateral placement of screws directly through the sacroiliac joint, and, finally, the substitution of bone graft into the joint, which subsequently fuses to stabilize the sacroiliac joint region.

To place stabilizing screws laterally in the sacroiliac joint region, a surgeon makes a secondary incision and drives screws through the external table of the iliac crest through the sacroiliac joint and into the sacrum. The trajectory of these screws is critical. If a surgeon places screws on a path too anterior, the screws may penetrate the sacral wall and damage the vessels that lie just beyond. If a surgeon places screws on a path too posterior, the screws may penetrate the sacral wall or sacral foramina and damage the nerves of the cauda aquina. Achieving and maintaining a precise trajectory can be difficult in the limited operating space. Therefore, a device to precisely guide the trajectory of the screws is optimal in a sacroiliac joint stabilization procedure.

SUMMARY OF THE INVENTION

The present invention provides a sacroiliac joint fusion alignment guide to allow accurate screw placement through the sacroiliac joint during a sacroiliac joint stabilization procedure. The sacroiliac joint fusion alignment guide is adjustable to allow use with varying patient anatomies. The sacroiliac joint fusion alignment guide includes a handle and two adjustable guidance arms for defining a trajectory for guiding screws and other instruments used in the sacroiliac joint stabilization procedure.

The first guidance arm has a substantially straight pronged distal end terminating in a first prong, a second prong and a space between the first prong and second prong defining a first point in a straight trajectory for inserting screws into a sacroiliac joint. The guidance arm forms a receiving bore on a distal end thereof to define a second point in the trajectory. The pronged distal end is inserted through a posterior incision in the patient into a cored-out sacroiliac joint, with the second guidance arm outside the body, and the orientation of the alignment guide is adjusted by pivoting the alignment guide about the pronged distal end to determine a suitable trajectory. Instruments are placed along the trajectory and guided by the alignment guide to drill screw holes and insert screws used in the sacroiliac joint fusion procedure into the screw holes.

According to one aspect of the invention, a sacroiliac joint fusion alignment guide is provided. The sacroiliac joint fusion alignment guide comprises a handle, a first guidance arm connected to the handle having a substantially straight pronged distal end terminating in a first prong, a second prong and a space between the first prong and second prong defining a first point in a straight trajectory for inserting screws into a sacroiliac joint and a second guidance arm coupled to the first guidance arm forming a receiving bore on a distal end thereof to define a second point in the trajectory.

According to another aspect of the invention, a method of guiding screws into a sacroiliac joint of a patient comprises the steps of inserting a pronged distal end of an alignment guide through a posterior incision in the patient into a cored-out sacroiliac joint and adjusting the orientation of the alignment guide to determine a suitable trajectory, defined by the alignment guide, for the screws, the trajectory extending from the sacroiliac joint through an iliac crest and out of the patient.

According to still another aspect of the invention, a method of guiding screws into a sacroiliac joint of a patient comprises the steps of providing an alignment guide comprising a handle, a first guidance arm having a distal end defining a first portion of a trajectory for inserting screws used to fuse the sacroiliac joint, and a second guidance arm having a distal end defining a second portion of the trajectory and using the alignment guide to insert screws along the trajectory and into the sacroiliac joint.

BRIEF DESCRIPTION OF THE FIGURES

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions

FIGS. 5A and 5B illustrates the handle of the sacroiliac joint fusion alignment guide of FIG. 2 according to one embodiment of the invention.

FIGS. 6A-6E illustrate the first guidance arm of the sacroiliac joint fusion alignment guide according to an illustrative embodiment of the invention.

FIGS. 7A-7E illustrate the second guidance arm of the sacroiliac joint fusion alignment guide according to an illustrative embodiment of the invention.

FIGS. 9A-9K illustrates the sacroiliac joint fusion alignment guide and related instruments during the steps shown in FIG. 8.

DETAILED DESCRIPTION OF THE INVENTION

Figure 1:
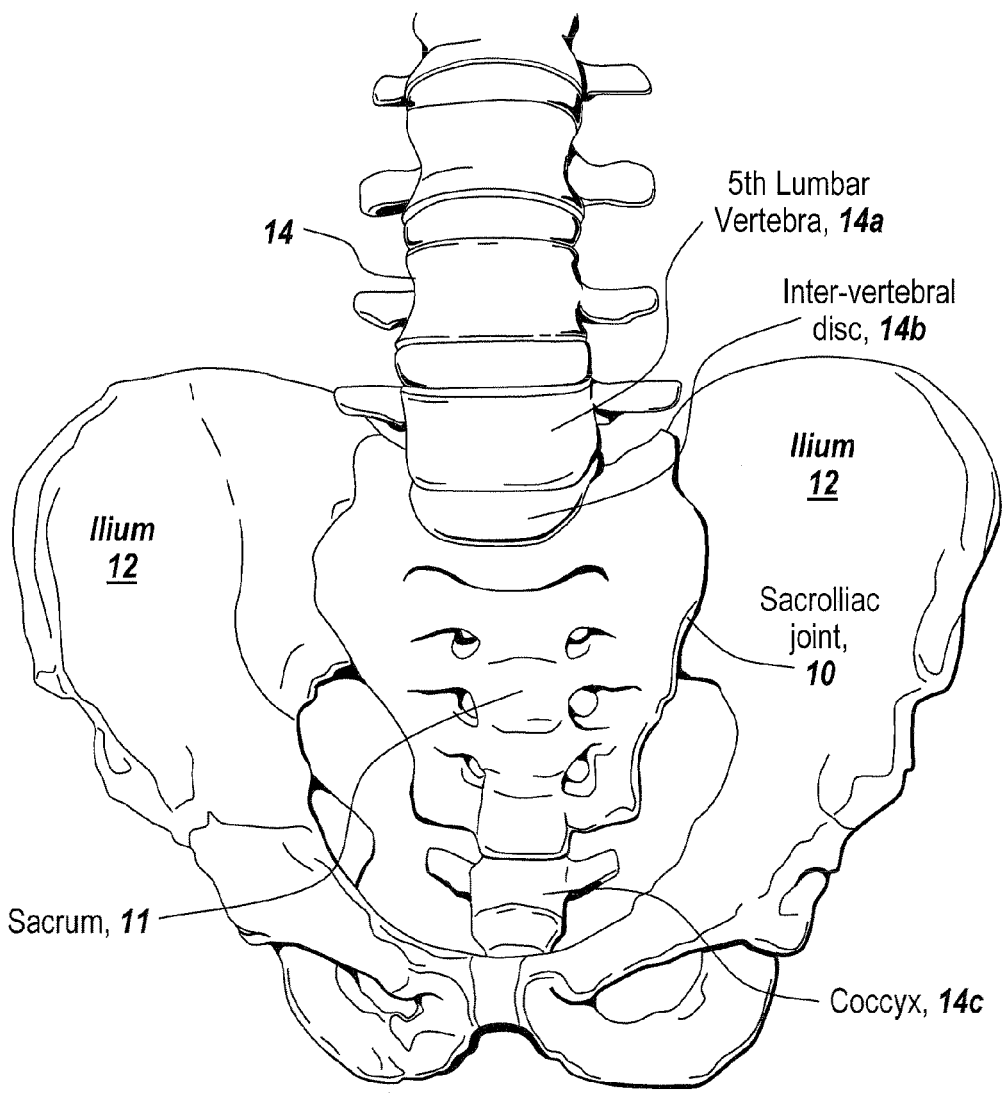
FIG. 1 illustrates the region of the human body containing the sacroiliac joint targeted using a sacroiliac joint fusion alignment guide of an illustrative embodiment of the invention.
Figure 2:
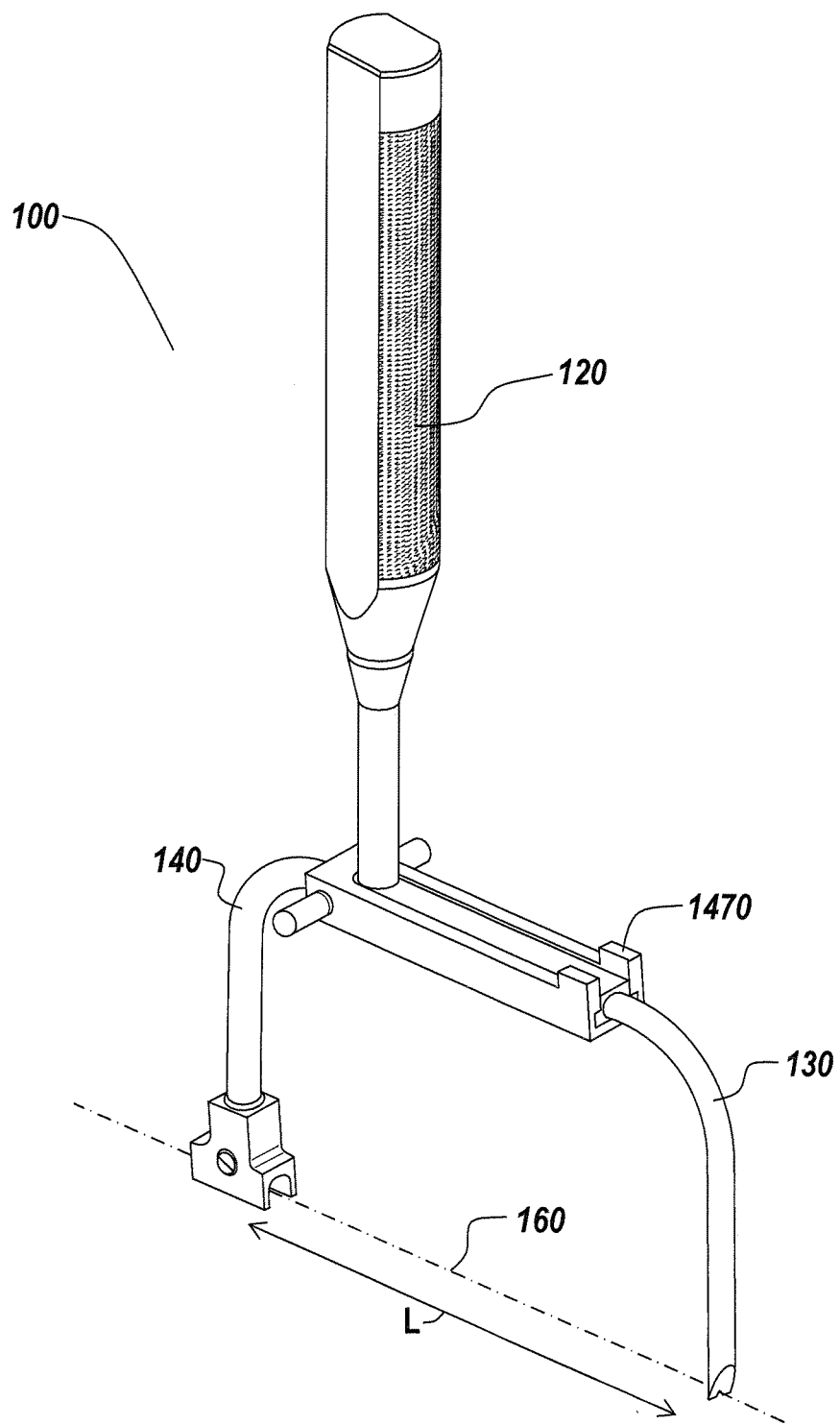
FIG. 2 illustrates an embodiment of a sacroiliac joint fusion alignment guide according to an illustrative embodiment of the invention.
Figure 3:
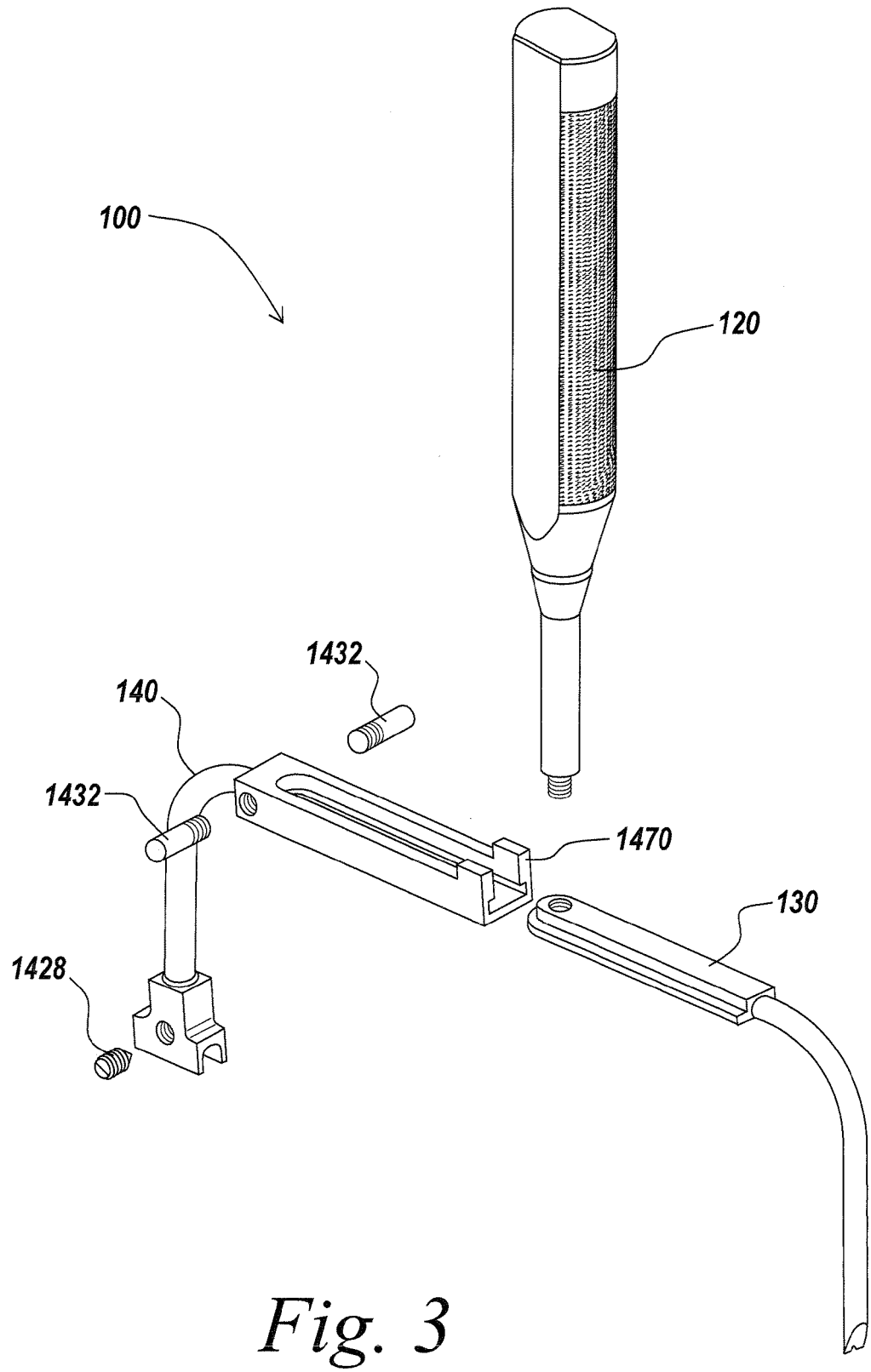
FIG. 3 is an exploded view of the sacroiliac joint fusion alignment guide of FIG. 2.
Figure 4B:
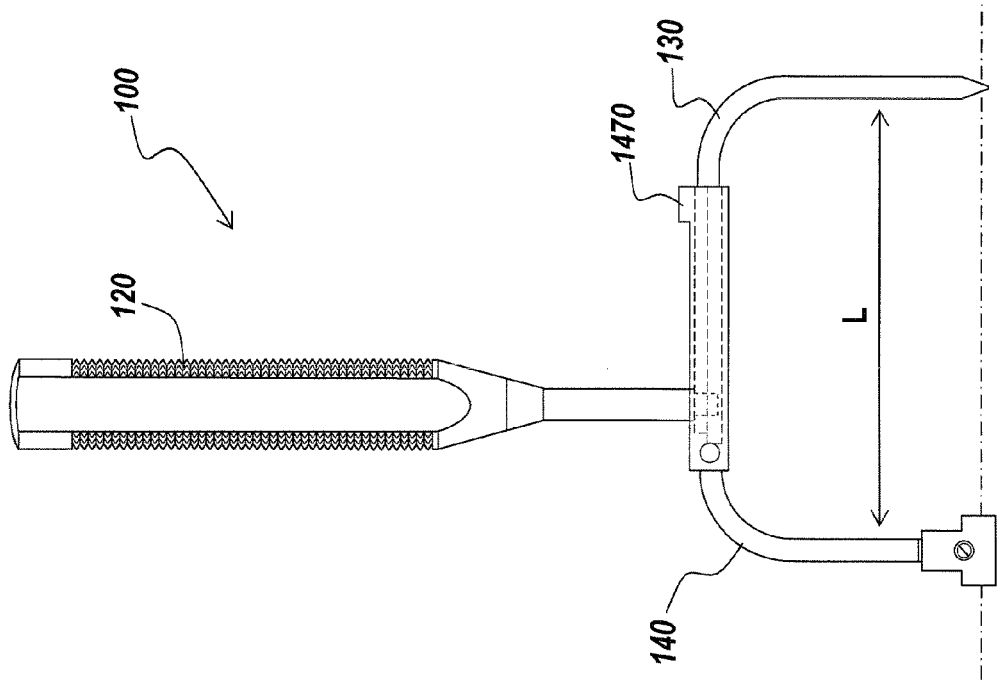
FIG. 4B is a side view of the sacroiliac joint fusion alignment guide of FIG. 2.
Figure 4A:
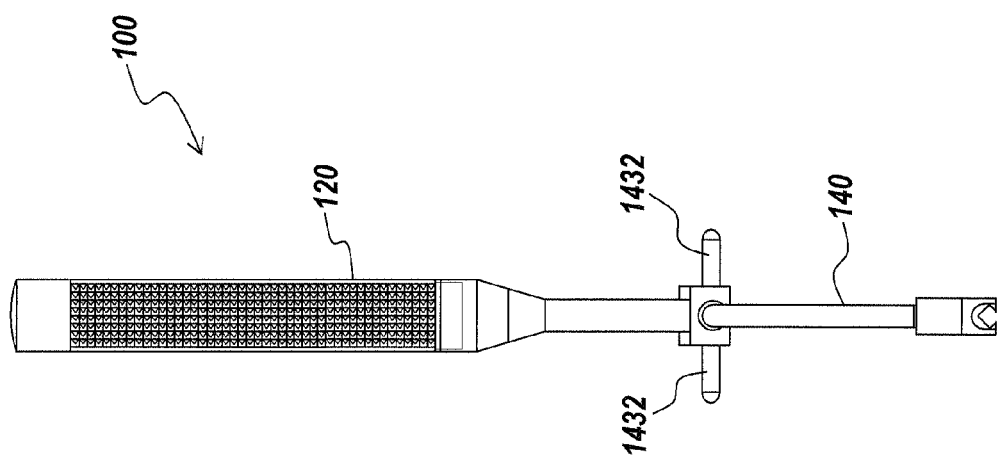
FIG. 4A is a front view of the sacroiliac joint fusion alignment guide of FIG. 2.

The present invention provides an improved surgical device and method for performing a sacroiliac joint fusion procedure. The present invention will be described below relative to certain exemplary embodiments in spinal surgery to provide an overall understanding of the principles of the structure, function, manufacture, and use of the instruments disclosed herein. Those skilled in the art will appreciate that the present invention may be implemented in a number of different applications and embodiments and is not specifically limited in its application to the particular embodiments depicted herein. For example, while the illustrative embodiment of the invention relates to a sacroiliac joint fusion alignment guide used in sacroiliac joint fusion surgery, the sacroiliac joint fusion alignment guide may be used in any surgical process where a trajectory is used to guide instruments to a surgical site.

FIGS. 2-4B illustrate an embodiment of a sacroiliac joint fusion alignment guide according to an illustrative embodiment of the invention. The illustrative sacroiliac joint fusion alignment guide 100 comprises a handle 120, a first guidance arm 130 for providing guidance to surgical devices at a distal end thereof, and a second guidance arm 140 for providing guidance to surgical instruments at a distal end thereof. The two guidance arms cooperate to define a straight trajectory 160 for guiding instruments and implements used in a sacroiliac joint fusion procedure or other surgical procedure. The first guidance arm 130 and the second guidance arm 140 slidably engage to allow device adjustment of the length L between the guidance arms 130 and 140 to accommodate different patient anatomies.

The handle 120, shown in detail in FIGS. 5A and 5B, may be removable coupled to the first guidance arm 130 and/or the second guidance arm 140. The handle 120 includes a gripping end 122 that a surgeon may hold and a coupling end 124. The coupling end 124 may include threads 125 or other suitable coupling means for coupling the handle 120 to one or both of the guidance arms 130 and/or 140. The coupling mechanism is not limited to the illustrative threads and may comprise any suitable coupling means.

As shown in detail in FIGS. 6A-6E, the first guidance arm 130 includes a pronged distal end 132 for defining the trajectory 160 and a male engagement proximal end 134. The pronged distal end 132 includes a first prong 1321 and a second prong 1322. The space 1324 in the notch between the first prong 1321 and second prong 1322, shown in FIG. 6E, defines a portion of the trajectory 160 for receiving and guiding instruments during a surgical procedure, such as a sacroiliac joint fusion procedure. The prongs 1321 and 1322 are preferably sized and dimensioned to receive a guidewire used in a sacroiliac joint fusion procedure in the space 1324 formed therebetween.

In the illustrative embodiment, pronged distal end 132 is tapered to facilitate insertion of the first guidance arm 130 into the sacroiliac joint 10. As shown in FIG. 6D, the distal end 132 includes surfaces 1325 and 1326 that taper to a point at the distal end. The pronged distal end 132 is preferably bent in a direction away from the male engagement proximal end 134. In the illustrative embodiment, the pronged distal end 132 extends substantially perpendicular to the male engagement proximal end 134, but one skilled in the art will recognize that the pronged distal end 132 and male engagement proximal end 134 may have any suitable orientation relative to each other. Preferably, the distal end 132 is substantially straight from the curved portion defining the transition between the distal end 132 and the male engagement proximal end 134 to facilitate insertion of the distal end 132 into relatively small incision.

The male engagement proximal end 134 of the first guidance arm includes a coupling means, illustrated as a threaded hole 341 on a top surface thereof for coupling to the handle 120. The coupling means may comprise any suitable means for receiving and/or coupling to the handle 120.

The male engagement proximal end 134 is also configured to movably couple to the second guidance arm 140. In the illustrative embodiment, the male engagement proximal end 134 includes an upper portion 1342 and a lower portion 1341 that is wider than the upper portion to define flanges 1341a, 1341b protruding from the sides along the length of the male engagement proximal end 134, as shown in FIG. 6C. The tip 1345 of the illustrative male engagement proximal end 134 of the first guidance arm 130 is rounded, but one skilled in the art will recognize that the tip 1345 can have any suitable configuration.

As shown in FIG. 7A-7E, the second guidance arm 140 of the sacroiliac joint fusion alignment guide 100 includes an attachment distal end 142 defining the trajectory 160 and a female engagement proximal end 144 for receiving the male engagement proximal end 134 of the first guidance arm 130. The attachment distal end 142 of the second guidance arm 140 includes a receiving bore 1421 configured to accept a shaft having an arbitrary cross-section defining a portion of the trajectory 160. The longitudinal axis of the receiving bore 1421 aligns with the trajectory 160. An obturator and/or another surgical instrument can pass through the receiving bore 1421 on the distal end of the second guidance arm 140, as described in detail below. A locking mechanism 1428 shown in FIG. 3, such as a set screw inserted in a locking bore 1429, may be used to lock an obturator within the receiving bore 1421. The receiving bore 1421 may have any suitable size and shape suitable for defining the trajectory and for guiding instruments during a surgical procedure. The receiving bore 1421 preferably has an open bottom end 1422 to allow movement of the guidance device 100 away from an instrument received in the receiving bore 1421.

The attachment distal end 142 is bent away from the axis of the female engagement proximal end 144. In the illustrative embodiment, the attachment distal end 142 extends substantially perpendicular to the female engagement proximal end 144, but one skilled in the art will recognize that the attachment distal end 142 and female engagement proximal end 144 may have any suitable orientation relative to each other.

Figure 7A:
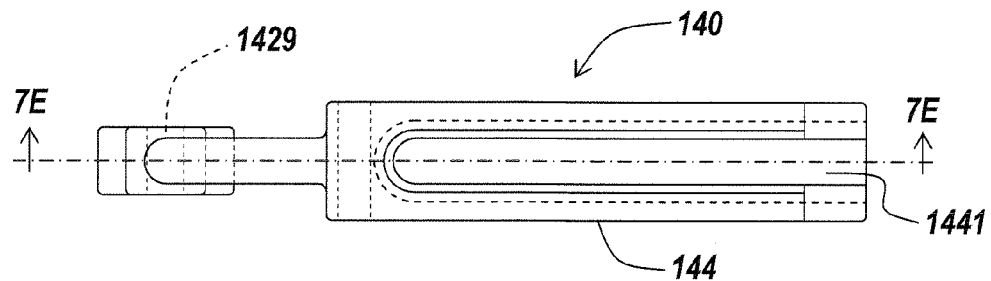
Figure 7B:
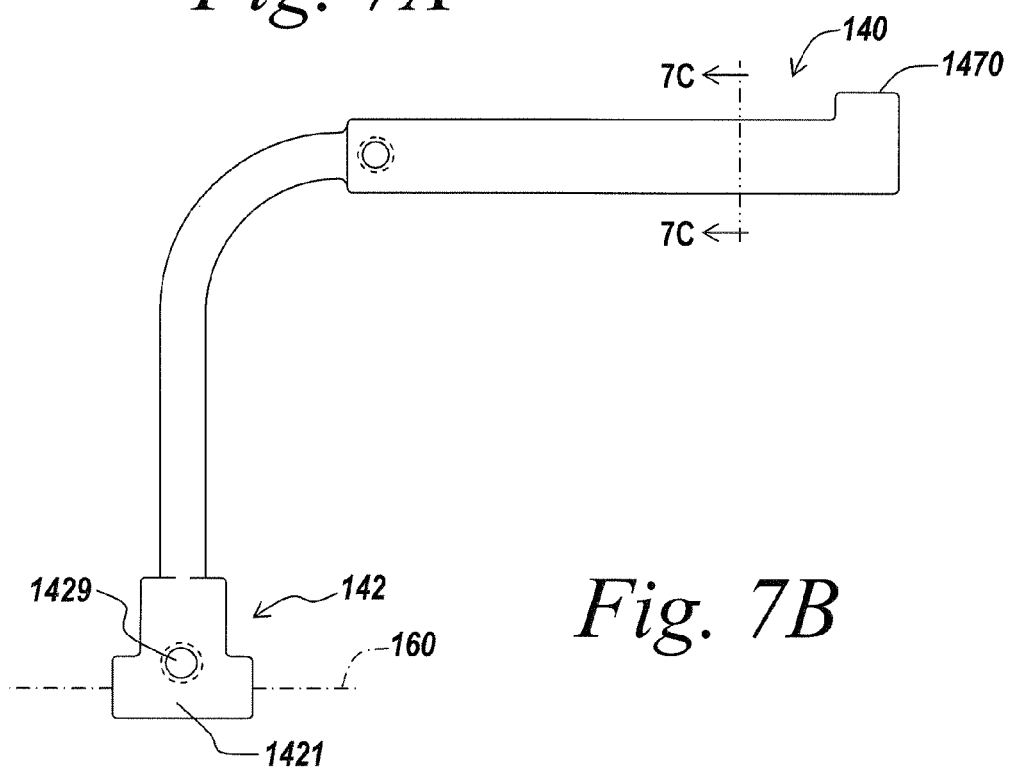
Figure 7C:
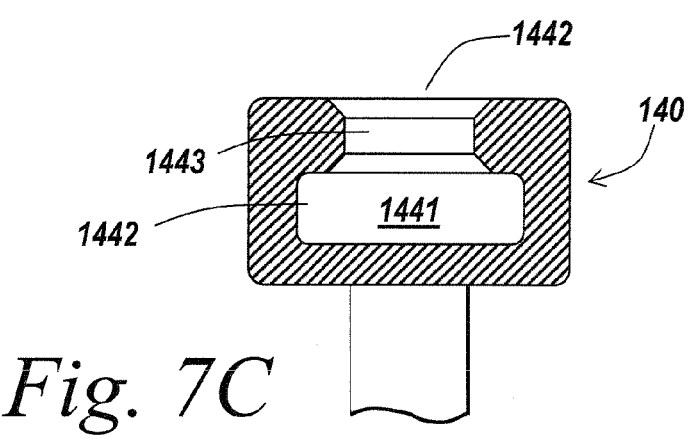

The first guidance arm 130 engages with the second guidance arm 140 via the male and female engagement proximal ends 134, 144, respectively. As shown in FIGS. 7A-7E, the female engagement proximal end 144 includes a slot 1441 sized and configured to receive the male engagement proximal end 134. The illustrative slot 1441 has an open top side 1442, a top portion 1443 and a bottom portion 1444 that is wider than the top portion, as shown in FIG. 7C, to receive the flanged bottom of the corresponding male engagement proximal end 134. The flanges 1341*a*, 1341*b* on the lower portion 1341 of the male engagement proximal end engage the side walls in the bottom portion 1444 of the receiving slot 1441 to guide the male engagement proximal end in the slot.

As shown in FIGS. 2-4B, the receiving bore 1421 aligns with the space 1324 of the prong distal end 132 to define two sections of the trajectory 160. The handle 120 attaches to the first guidance arm 130 and may provide a means to manipulate the first guidance arm 130 within the second guidance arm 140, and also to lock the position of the first guidance arm relative to the second guidance arm. In one embodiment, the handle 120 rotates about its axis to loosen and/or tighten the connection between the guidance arms and/or between the handle 120 and the guidance arms.

A ratcheting means or other device may be used to control the distance L between the two guidance arms. Alternatively, an infinite number of relative positions may be provided by sliding the guidance arms relative to each other.

Guiding posts 1432 are provided to allow ease of translation between guidance arms 130 and 140. For example, the guide may be gripped to facilitate translation of the first guidance arm 130 relative to the second guidance arm 140. Other guide mechanisms may be provided in place of the guide posts.

Other suitable means for movably coupling the first and second guidance arms 130, 140 may be used.

The second guidance arm (or the first guidance arm) may contain a stop to prevent the guidance arms from separating when the handle is in place. For example, the illustrative second guidance arm 140 includes a protrusion 1470 at the proximal end of the female engagement proximal end 144 that prevents the corresponding first guidance arm 130 from pulling entirely out of the slot 1441 when the handle coupling end 124 engages the threaded hole 341 in the first guidance arm 130.

Figure 8:
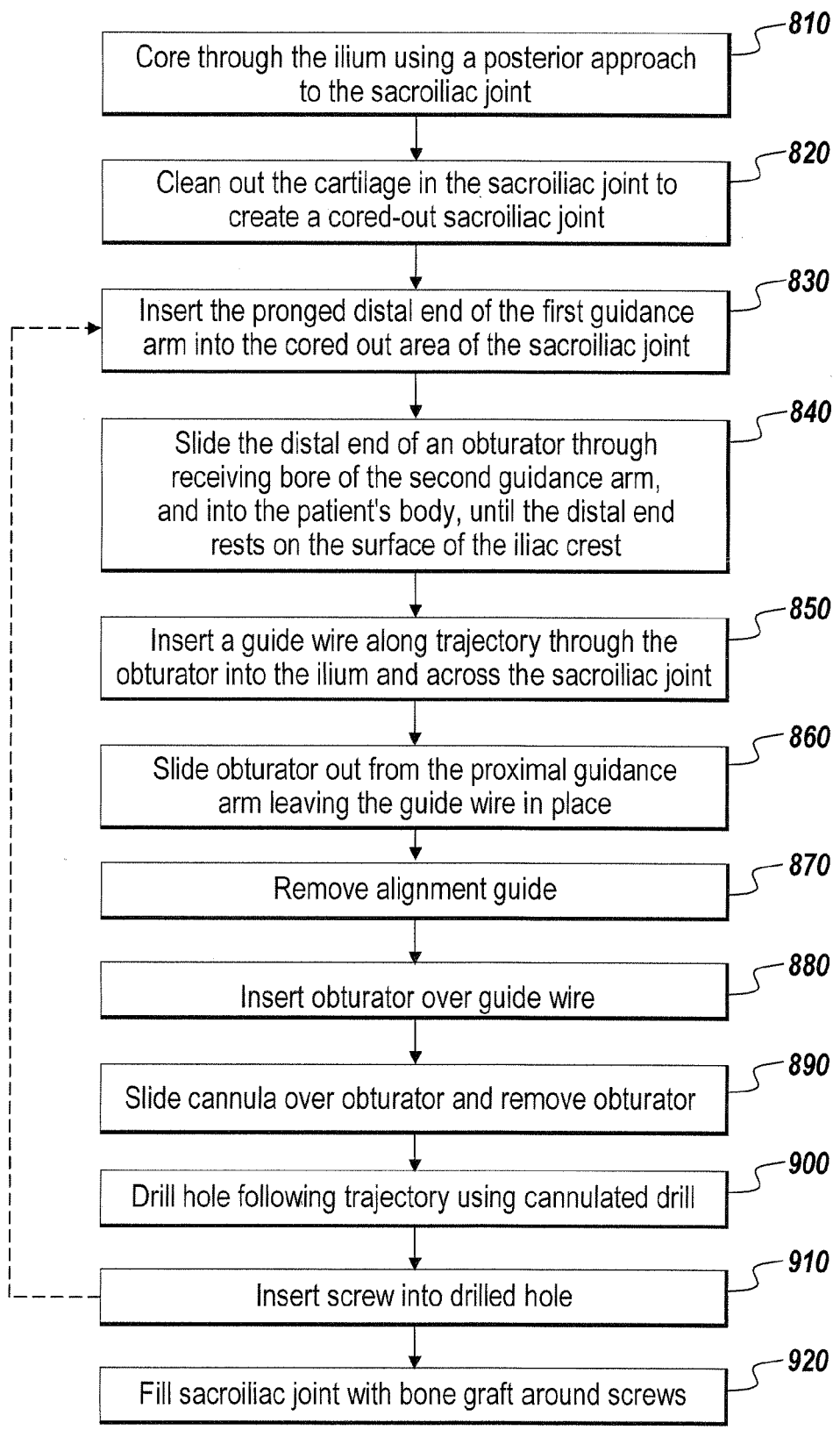
FIG. 8 is a flow chart illustrating a sacroiliac fusion procedure using a sacroiliac joint fusion alignment guide according to an illustrative embodiment of the invention.

FIG. 8 illustrates the steps involved in performing a sacroiliac joint fusion procedure using the alignment guide 100 according to an illustrative embodiment of the invention. FIGS. 9A-9K illustrates the sacroiliac joint fusion alignment guide and related instruments during the steps shown in FIG. 8.

Figure 9C:
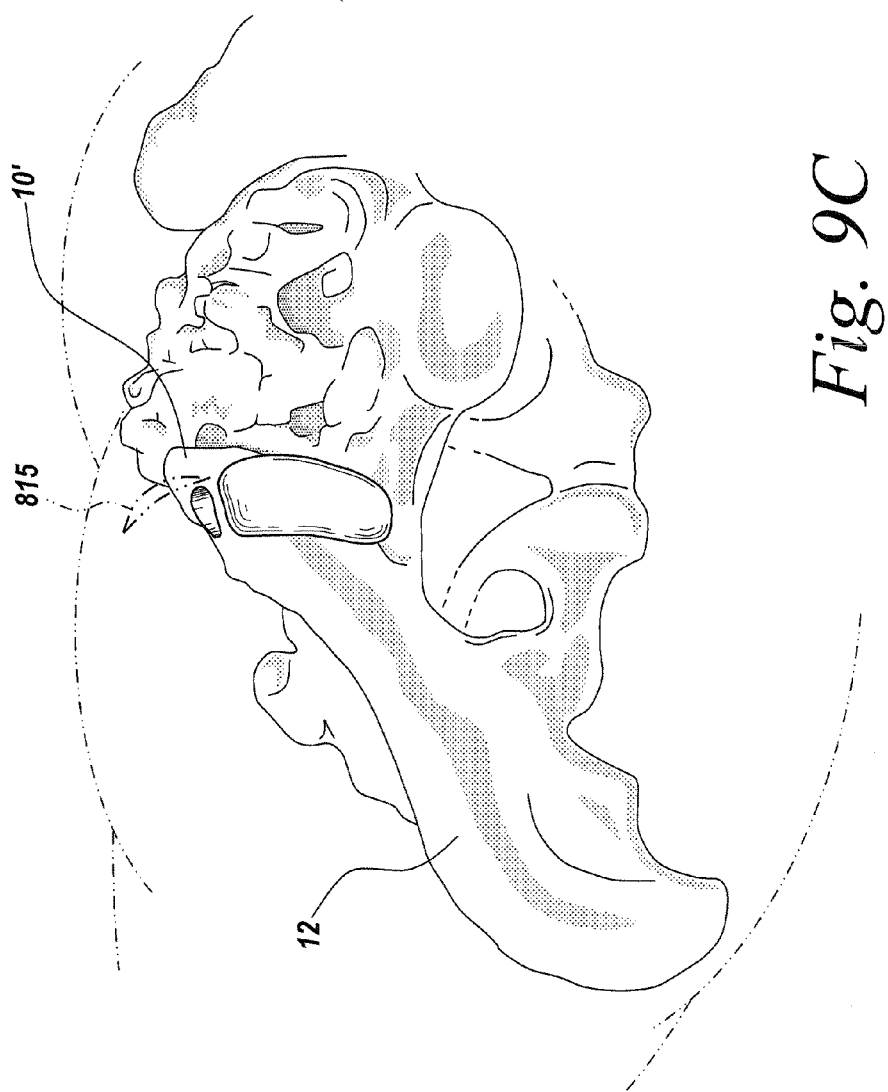

The sacroiliac joint is first prepared for the sacroiliac joint fusion procedure in steps 810 and 820. In a first step 810, shown in FIG. 9A, a surgical coring instrument 811 is used to core through the ilium 12 using a posterior approach to the sacroiliac joint 10 through an incision 815. In step 820, shown in FIG. 9B, the same or a different surgical tool 811 is used to clean out the cartilage in the sacroiliac joint to create a cored-out sacroiliac joint 10', as shown in FIG. 9C.

After preparing the sacroiliac joint 10, in step 830, the pronged distal end 132 of the first guidance arm 130 is inserted through the incision 815 into the cored out area of a sacroiliac joint 10', as shown in FIG. 9D. The second guidance arm 140 is located outside the patient's body to define the trajectory 160 extending laterally from the sacroiliac joint 10' outside the body. Preferably, the pronged distal end 132 contacts but is not fixed or attached to the sacrum 11, ilium, or sacroiliac joint 10' to allow for the movement of the distal end of the second guidance arm 140 relative to the distal end of the first guidance arm 130 in multiple degrees of freedom. For example, alignment guide 10 may be maneuvered and pivoted about the pronged distal end 132 by the surgeon to find a proper trajectory 160 from the distal end of the second guidance arm 140 to the pronged distal end of the first guidance arm 130 inserted in the sacroiliac joint. Likewise, the distal end 132 of the first guidance arm 130 may be maneuvered within the sacroiliac joint 10' to find a proper trajectory. After determining the proper trajectory, the surgeon holds the alignment guide in place during subsequent steps.

Once the surgeon has selected the proper trajectory, the surgeon may deliver one or more instruments along the trajectory to prepare for positioning one or more bone anchors through the sacroiliac joint and may subsequently insert one or more bone anchors along the trajectory to fix the sacrum to the ilium at the sacroiliac joint. The following steps provide one exemplary method of preparing for and placing bone anchors at the sacroiliac joint. One of ordinary skill in the art will recognize some of the exemplary steps may be deleted, or occur in alternative order or additional conventional surgical steps may be added.

Figure 9E:
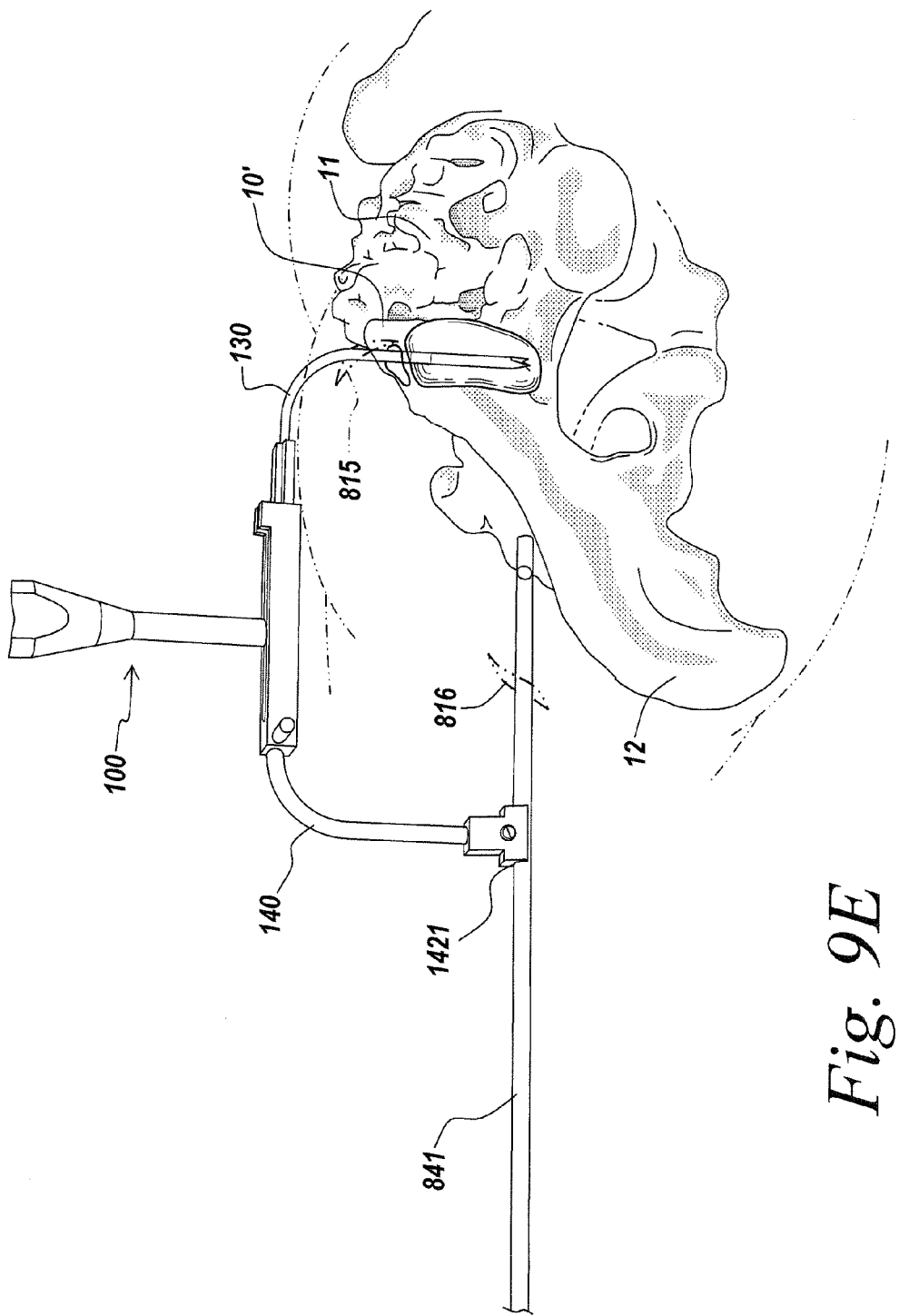
Figure 9F:
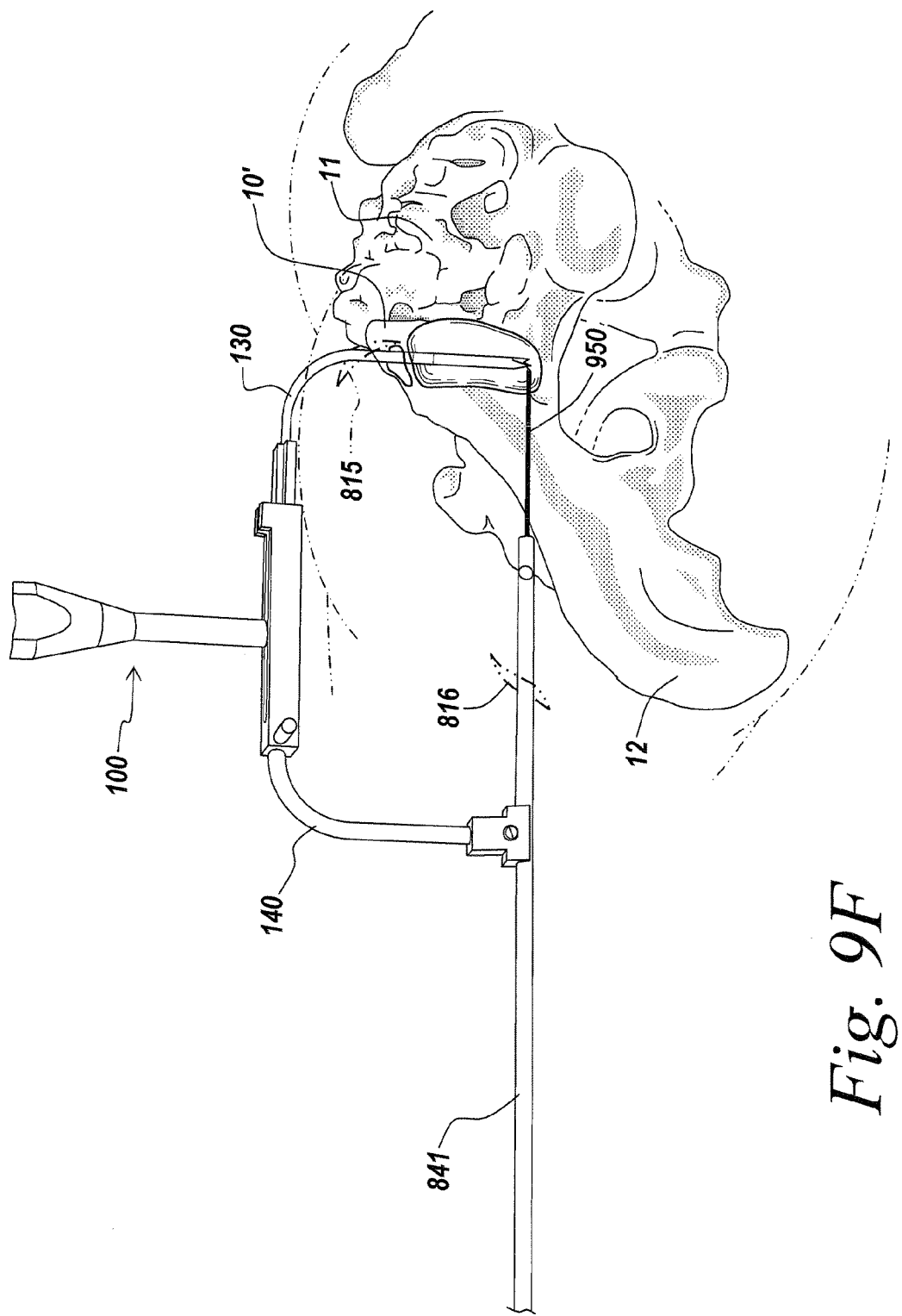
Figure 9G:
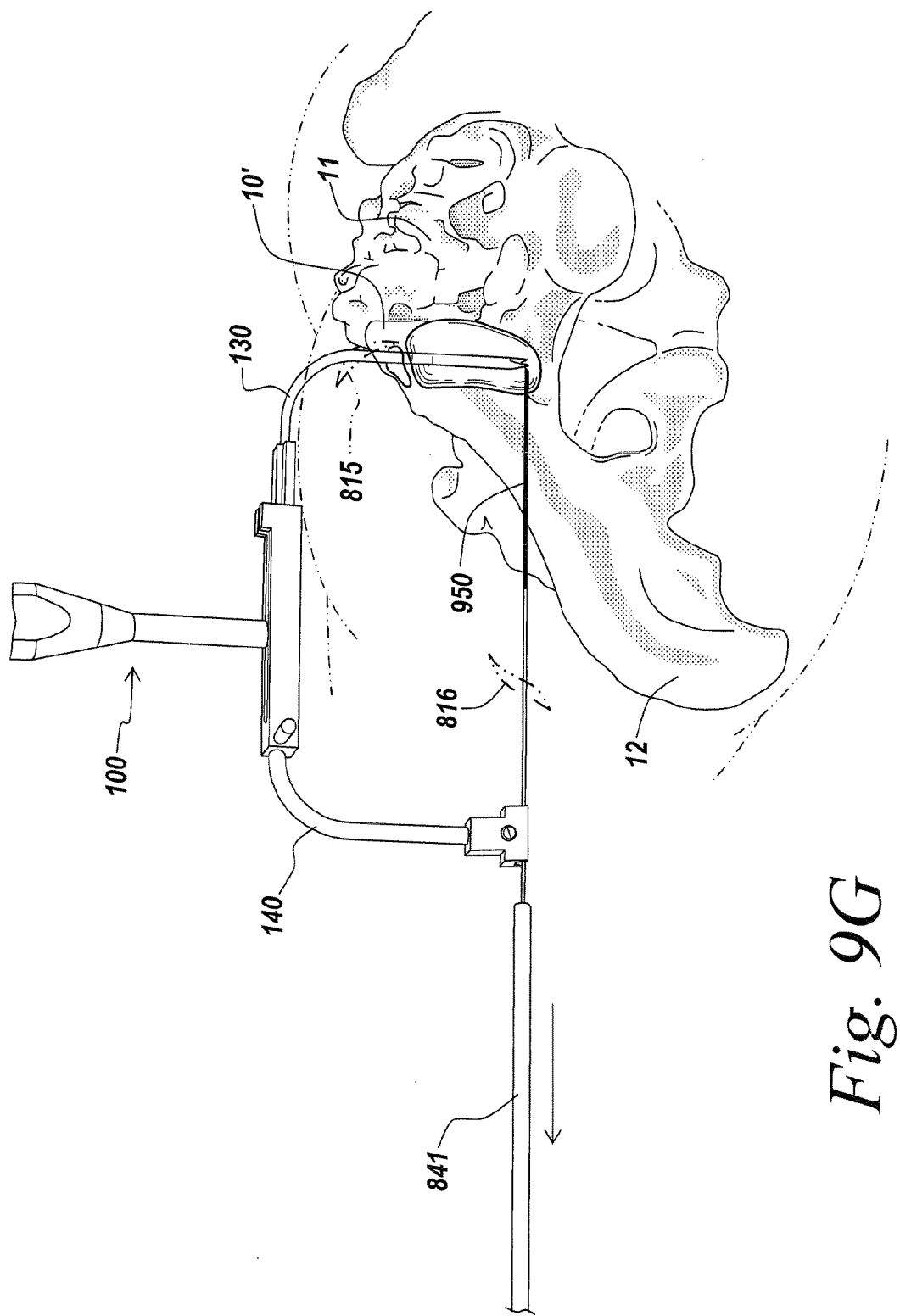

In step 840, shown in FIG. 9E, the distal end of an obturator 841, or other selected surgical instrument, slides through the receiving bore 1421 of the second guidance arm 140 and passes through a lateral incision 816 into the patient's body, until the distal end rests on the surface of the iliac crest. Due to the configuration of the alignment guide 100, the obturator 841 extends and slides along the trajectory 160 defined by the alignment guide 100.

Preferably, the obturator 841 is cannulated and oriented so that a guidewire can pass through a passage therein into the iliac crest through the sacroiliac joint 10 and into the sacrum 11 in the trajectory of the screw placement. In step 850, a guidewire 950 is then inserted through the obturator 841 into the ilium and across the sacroiliac joint 10, shown in FIG. 9F. The guidewire 950 is inserted to a desired depth by reading index marks corresponding to the obturator 841. In step 860, shown in FIG. 9G, the obturator 841 is slid out from the proximal guidance arm 140 of the alignment guide, leaving the guidewire 950 in place, such that the guidewire 950 extends from the sacroiliac joint 10 out of the patient's body along the selected trajectory 160.

Figure 9H:
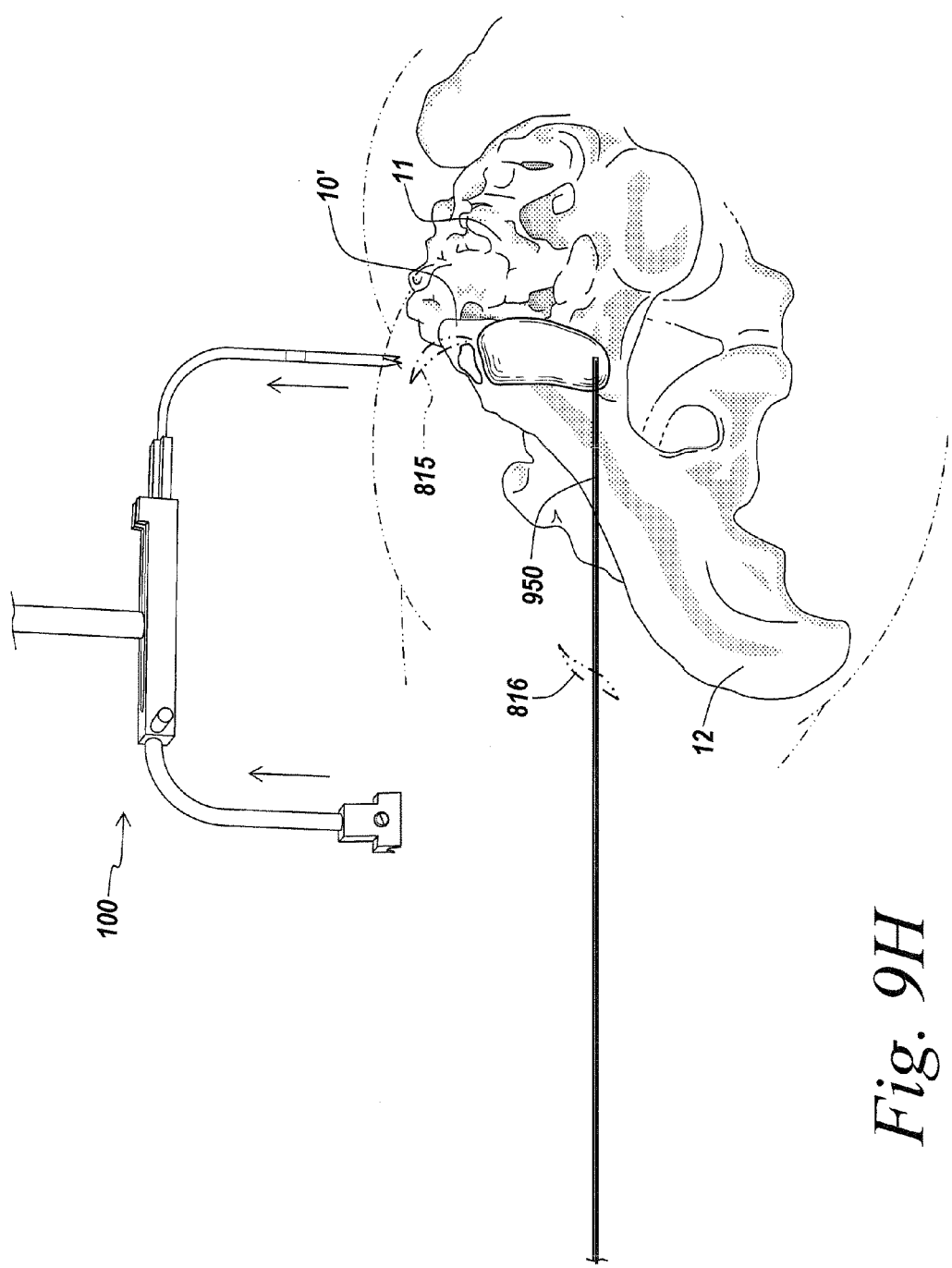

In step 870, the alignment guide 100 may be removed, as shown in FIG. 9H, by pulling the alignment guide 100 in a direction away from the guidewire 950, leaving the guidewire in place. The guidewire 950 passes through the bottom opening 1422 in the receiving bore 1421 of the second guidance arm 140 and from the pronged distal end 132 of the first guidance arm 130 as the alignment guide 100 is removed.

Figure 9I:
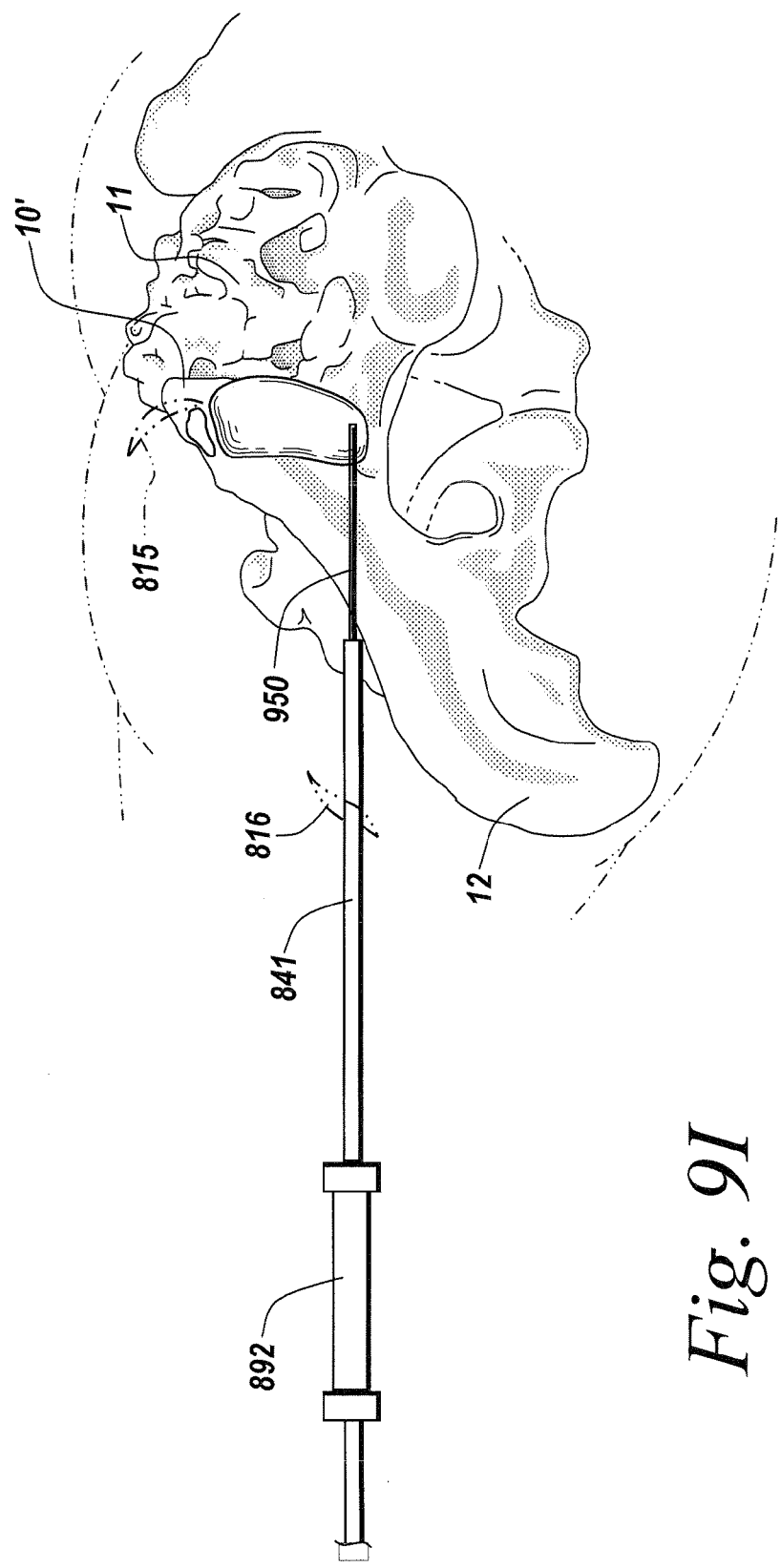

In step 880, the obturator 841 may be re-inserted along the trajectory 160 into the wound over the guidewire 950 defining the trajectory 160. In step 890, a first cannula 892 slides into position over the inserted obturator 841 and the obturator 841 is removed, as shown in FIG. 9I. Then, in step 900, a cannulated drill, having a drill stop is attached thereto and set to a desired depth, is inserted over the guidewire 950, and through the cannula 892, and drills a screw hole 906 along the trajectory 160 to the preset depth through the iliac crest 11 into the sacroiliac joint 10', as shown in FIG. 9I.

Figure 9J:
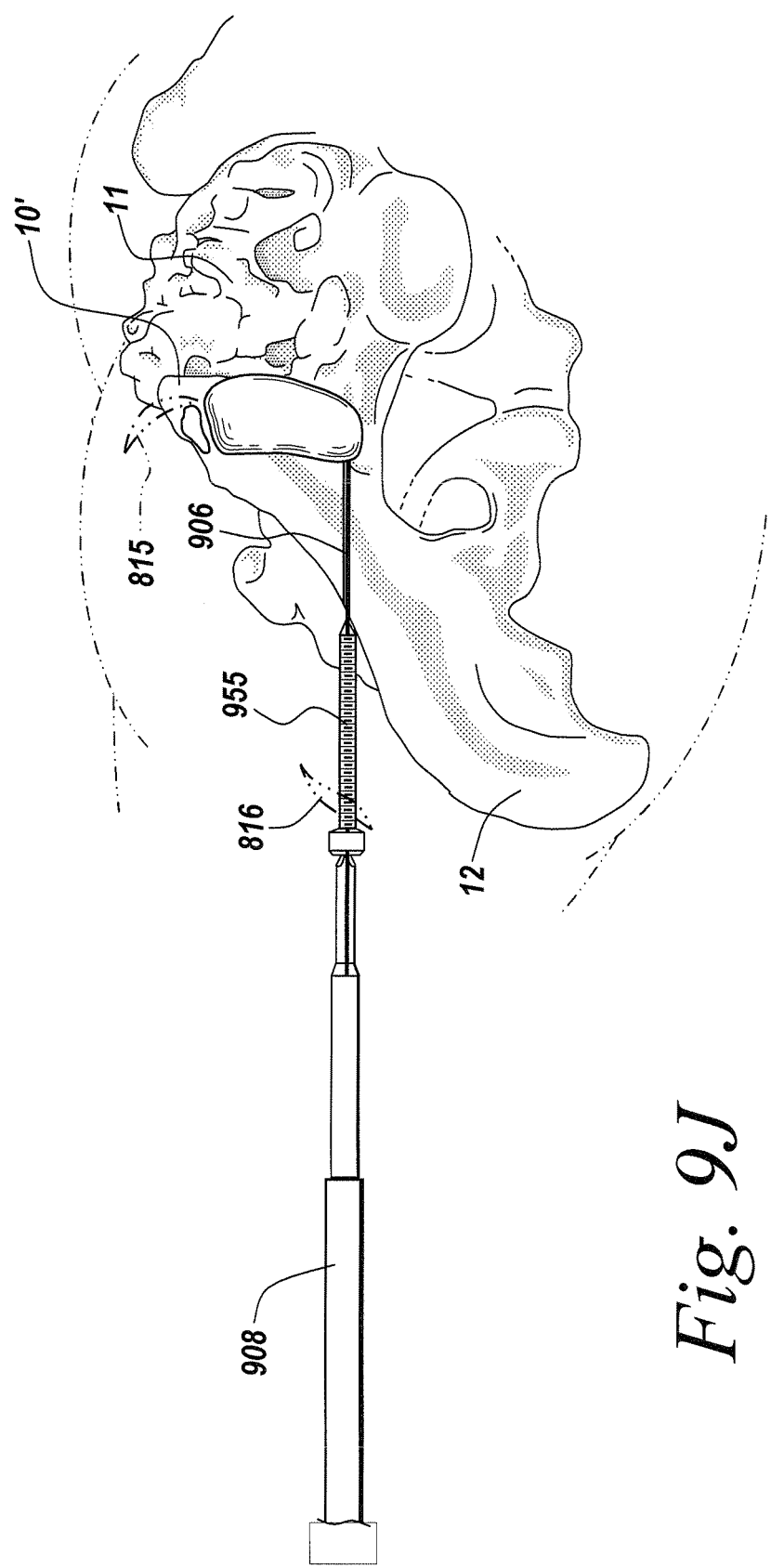

In step 910, a first screw 955 is inserted into the iliac crest through the sacroiliac joint 10 and into the sacrum 11 along the trajectory 160 defined by the guidewire 950, as shown in FIG. 9J. The screw may be inserted by removing the drill and cannula and inserting the screw 955 on a self-retaining screwdriver 908. The screw 955 is then inserted over the guidewire 950 and into the screw hole 906. The guidewire 950, precisely placed using the alignment guide, precisely guides the trajectory of the screw 955 during placement. During drilling, the surgeon can place dilators over the obturator to protect the soft tissue.

Steps 830-910 may be repeated for a multiple screws 956, shown in FIG. 9K, which is placed along a second trajectory 170 defined using the alignment guide 100, as described above. After insertion of the screws 955 and 956, the surgeon may fill or pack the sacroiliac joint with bone graft 990 around the screws 955 and 956 cause fusion of the sacroiliac joint 10 in step 920.

Figure 10:
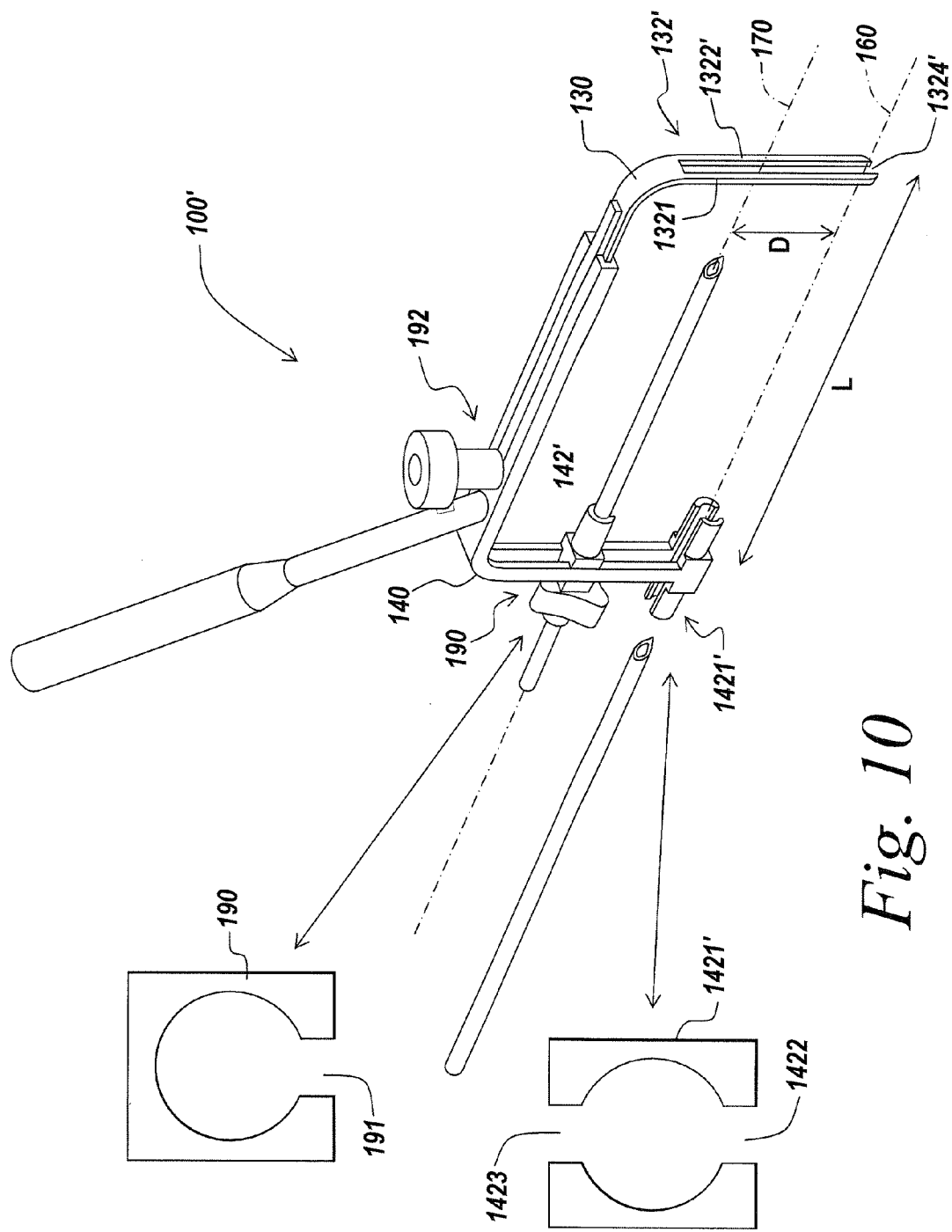
FIG. 10 illustrates a sacroiliac joint fusion alignment guide according to another embodiment of the invention.

According to another embodiment of the invention, shown in FIG. 10, a sacroiliac joint fusion alignment guide 100' may include an adjustable attachment piece 190 defining a second trajectory 170 with an adjustment knob 192 on the second guidance arm 140. The rigid receiving bore 1421' on the distal end of the second arm 140 may be split to form both a bottom opening 1422 and an upper opening 1423 to allow removal of the alignment guide 100' once more than one guidewire is placed. As shown, the prongs 1321', 1322' on the pronged distal end 132' of the first guidance arm 130 are longer than the embodiment shown in FIGS. 2-7, such that the space 1324' between the prongs 1321', 1322' aligns with both the receiving bore 1421' and the adjustable attachment piece 190. The illustrative attachment piece 190 has an open bottom end 191 to allow removal of the alignment guide 100' over surgical implements, such as a guidewire. The adjustment knob 192 allows for adjustment of the distance D between the trajectory 160 defined by the lower receiving bore 1421' and the trajectory 170 defined by the attachment piece 190.

During a fusion procedure using the alignment guide 100' of FIG. 10, a first guidewire may be inserted using the instruments and trajectory 160 between the lower receiving bore 1421' and the pronged distal end 132' as described above with respect to FIG. 8. A second guidewire may be inserted along the trajectory 170 defined by the adjustment piece 190 and the pronged distal end 132'. To insert the second guidewire, a second obturator is placed through the adjustable attachment piece 190 until the obturator rests on the surface of the iliac crest. The second guidewire is then inserted through the sacroiliac joint along the trajectory 170. The alignment guide 100' is then removed by pulling the alignment guide 100' in a direction perpendicular and away from the two inserted guidewires, leaving the guidewires and obturators in place, all of which extend along and define one of the trajectories 160 or 170. Then, screw holes are drilled along the trajectories 160 and 170 through the iliac crest into the sacroiliac joint using a cannulated drill passed over the guidewires. Dilators may be placed over the obturators prior to removal to protect soft tissue during the drilling procedure. A screw is then inserted over each guidewire and placed into the iliac crest through the sacroiliac joint and into the sacrum along the corresponding trajectory. Then, as described above, the sacroiliac joint is packed with bone graft around the screws.

The sacroiliac joint fusion alignment guide of the illustrative embodiments of the invention provides a precise trajectory for guiding surgical tools and implants during a surgical procedure, while allowing degrees of freedom to facilitate determination of an optimal orientation for the trajectory. The pronged distal end of the first guidance arm may be easily inserted into a small space in the sacroiliac joint, allowing maneuverability of the alignment guide to determine a suitable trajectory. The design of the guide also accommodates multiple patient anatomies and allows the surgical procedure to be performed in a minimally invasive manner thereby reducing tissue trauma and blood loss while minimizing incision size.

The present invention has been described relative to an illustrative embodiment and application in spinal correction surgery. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. A method of guiding screws into a sacroiliac joint of a patient, comprising the steps of:
    inserting a distal end of an alignment guide through a posterior incision in the patient into a cored-out sacroiliac joint wherein the distal end of the alignment guide is pronged and dimensioned to receive a guidewire and wherein the distal end of the alignment guide includes a first prong and a second prong and a space between the first prong and the second prong defining a point for inserting a screw in the sacroiliac joint and wherein the alignment guide has a guidance arm at the distal end and a guidance arm at the proximal end;
    adjusting a distance between the guidance arms of the alignment guide to accommodate patient anatomy; and
    adjusting the orientation of the alignment guide to define a suitable trajectory for the screws by pivoting the alignment guide about the pronged distal end of the alignment guide, the trajectory extending from the sacroiliac joint through an iliac crest and out of the patient.

2. The method of claim 1, wherein the alignment guide is adjusted in multiple degrees of freedom to select a suitable trajectory.

3. The method of claim 1, further comprising the step of inserting a guidewire along the trajectory defined by the alignment guide, such that the guidewire extends from the sacroiliac joint along the trajectory and out of the patient.

4. The method of claim 3, wherein the step of inserting the guidewire comprises the steps of:
    inserting an obturator through a receiving bore on the guidance arm at the proximal end on the alignment guide, wherein the receiving bore aligns with the distal end of the alignment guide to define the trajectory;
    inserting the guidewire through the obturator; and
    removing the obturator from the alignment guide; and
    removing the alignment guide, leaving the guidewire extending from the sacroiliac joint along the trajectory and out of the patient.

5. The method of claim 3, further comprising the step of drilling a screw hole into the sacroiliac joint following the trajectory using a cannulated drill inserted over the guidewire.

6. The method of claim 5, further comprising the step of inserting a screw into the drill hole.

* * * * *